US00PP23329P3

(12) United States Plant Patent
Ranney

(10) Patent No.: US PP23,329 P3
(45) Date of Patent: Jan. 15, 2013

(54) PEARLBUSH PLANT NAMED 'BLIZZARD'

(50) Latin Name: *Exochorda serratifolia×macrantha (racemosa×korolkowii)*
Varietal Denomination: Blizzard

(75) Inventor: Thomas G. Ranney, Arden, NC (US)

(73) Assignee: North Carolina State University, Raleigh, NC (US)

( * ) Notice: Subject to any disclaimer, the term of this patent is extended or adjusted under 35 U.S.C. 154(b) by 110 days.

(21) Appl. No.: 12/927,738

(22) Filed: Nov. 22, 2010

(65) Prior Publication Data

US 2012/0131710 P1 May 24, 2012

(51) Int. Cl.
*A01H 5/00* (2006.01)

(52) U.S. Cl. ..... Plt./226

(58) Field of Classification Search ..... Plt./226, Plt./263.1

See application file for complete search history.

*Primary Examiner* — Kent L Bell

(74) *Attorney, Agent, or Firm* — Michael Best & Friedrich LLP

(57) ABSTRACT

'Blizzard' is a new pearlbush plant particularly distinguished by its compact habit, smaller plant height and width, larger flower diameter, and larger genome size.

2 Drawing Sheets

Genus and species: *Exochorda serratifolia×macrantha* (*racemosa×korolkowii*).

Variety denomination: 'Blizzard'.

BACKGROUND OF THE NEW PLANT

The present invention comprises a new and distinct variety of *Exochorda*, botanically known as *Exochorda*, and hereinafter referred to by the variety name 'Blizzard'. This new pearlbush shrub was developed through a breeding program in Mills River, N.C. 'Blizzard' is an $F_2$ hybrid between the unnamed female parent, *Exochorda serratifolia* NCSU 2000-088 (unpatented) and the male parent, *Exochorda×macrantha* (*racemosa×korolkowii*) 'The Bride' NCSU 1999-188 (unpatented). The first asexual propagation of 'Blizzard' was carried out in the summer of 2003 by rooting stem cuttings in Mills River, N.C. and has been asexually reproduced repeatedly by vegetative cuttings in North Carolina over a 7 year period.

'Blizzard' roots readily from softwood cuttings from juvenile plants treated with a basal dip of 5,000 ppm indole butyric acid (potassium salt) in water. 'Blizzard' has been found to retain its distinctive characteristics through successive asexual propagations via vegetative cuttings.

Plant Breeder's Rights for this variety have not been applied for. 'Blizzard' has not been made publicly available or sold more than one year prior to the filing date of this application.

SUMMARY OF THE INVENTION

The following are the most outstanding and distinguishing features of this new variety when grown under normal horticultural practices in Mills River, N.C.

1. A compact shrub habit;
2. Upright to rounded form;
3. Extremely floriferous with large flowers; and 4. A polyploid cytotype with a relative 2C genome size of approximately 2.2 pg.

DESCRIPTION OF THE PHOTOGRAPHS

This new pearlbush variety is illustrated by the accompanying photographs which show the plant's form, foliage and flowers. The colors shown are as true as can be reasonably obtained by conventional photographic procedures. The photographs were taken in Mills River, N.C.

DESCRIPTION OF THE NEW VARIETY

Figure 1:
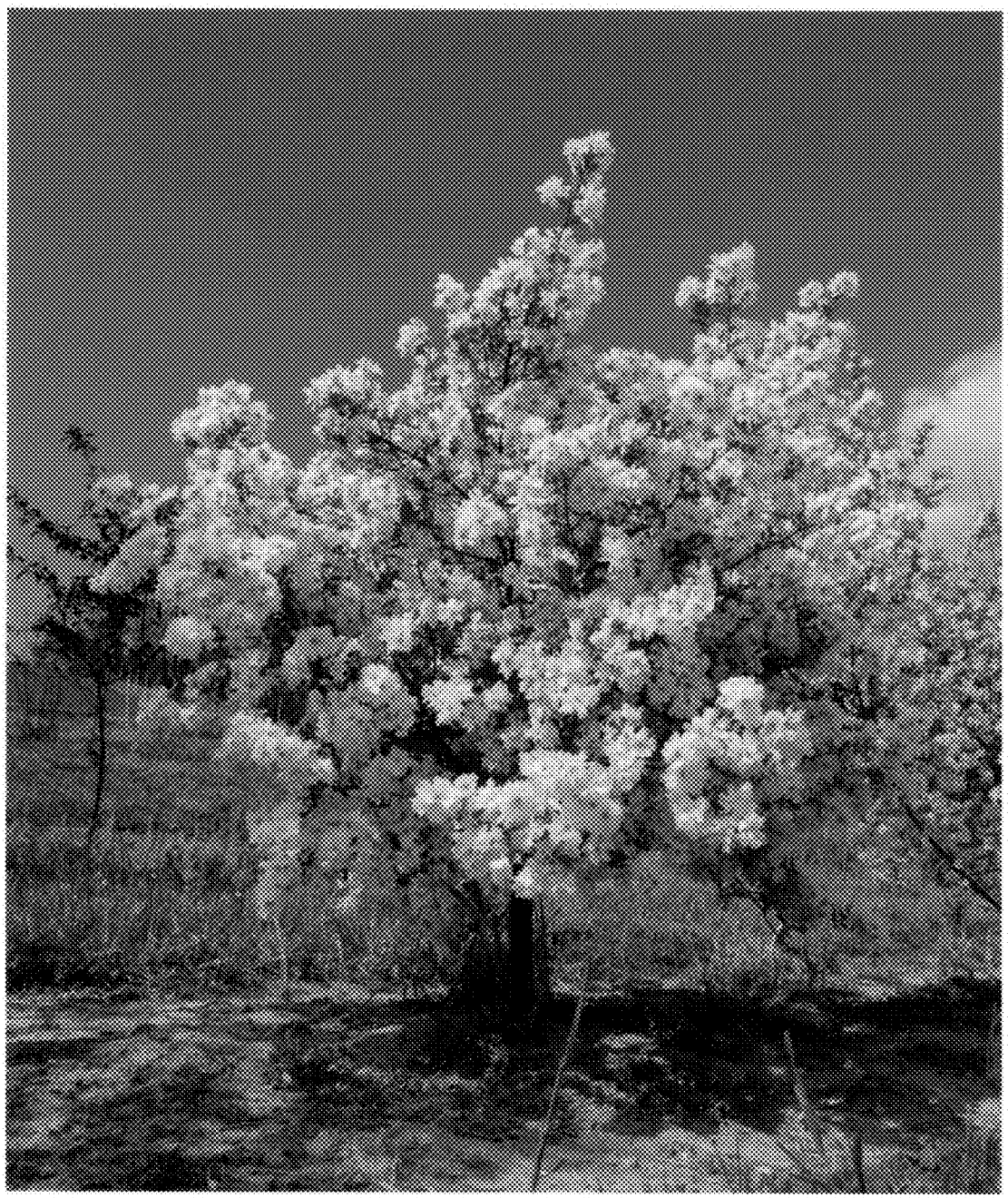
FIG. 1 shows a 6 year old, field-grown plant in full bloom in April, 2008.
Figure 2:
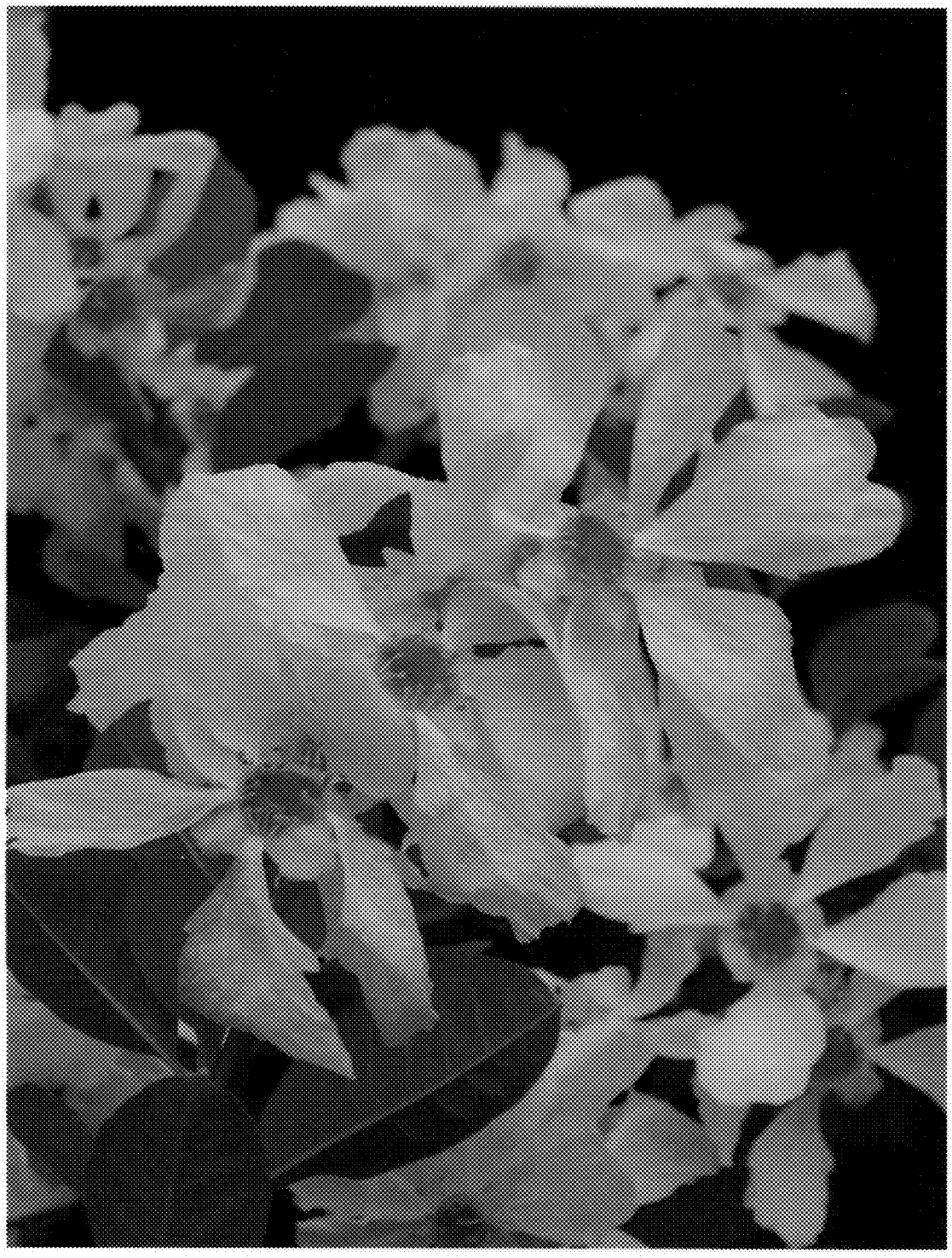
FIG. 2 shows the flowers of a greenhouse-grown plant in April, 2009.

The following detailed description sets forth the distinctive characteristics of 'Blizzard'. The detailed description was taken on 6-year-old plants growing under landscape conditions in Mills River, N.C. in April 2008. Color references are to The R.H.S. Colour Chart of The Royal Horticultural Society of London (R.H.S.), 2001 Edition.

DETAILED BOTANICAL DESCRIPTION OF THE PLANT

Classification:

*Botanical name.*—*Exochorda.*

*Common name.*—Pearlbush.

Parentage: An $F_2$ hybrid was made between the following parents.

*Female parent.*—Unnamed plant *Exochorda serratifolia* NCSU 2000-088 (unpatented).

*Male parent.*—*Exochorda×macrantha* 'The Bride' (unpatented).

Plant description:

*Growth habit.*—Compact.

*Plant shape.*—Upright when young, eventually becoming rounded with age.

*Height at maturity.*—1.2 meters to 1.5 meters.
*Width at maturity.*—1.2 meters to 1.5 meters.

Lateral branches:
*Number.*—Average is 9 (range is 6 to 15).
*Length.*—Average is 66.6 cm (range is 10.0 cm to 120.0 cm).
*Diameter.*—Average 1.4 cm (range is 0.4 cm to 2.8 cm).
*Internode length.*—Average is 7.5 cm (range is 1.0 cm to 21.0 cm).
*Immature color.*—RHS 144A (Yellow-green).
*Mature color.*—RHS 199A to 201A (Greyed Brown).
*Immature texture.*—Glabrous and slightly fissured.
*Mature texture.*—Strongly fissured and woody.

Stem:
*Mature stem color.*—RHS N200A (Brown).
*Immature stem color.*—RHS 143A (Yellow-green).

Leaves:
*Type.*—Deciduous.
*Arrangement.*—Alternate.
*Shape.*—Obovate to obelliptic.
*Apex.*—Obtuse mucronulate.
*Base.*—Cuneate.
*Margin.*—Entire occasionally serrate towards apex.
*Mature leaf size.*—Length: Average is 5.12 cm (range is 4.8 cm to 5.6 cm). Width: Average is 2.92 cm (range is 2.6 cm to 3.3 cm).
*Immature leaf color.*—Adaxial (upper) surface: Flushes RHS 143A (Green), which changes to RHS 137A (Green). Abaxial (lower) surface: RHS 144A (Yellow-green) which changes to RHS 137A (Green).
*Mature leaf color.*—Adaxial (upper) surface: RHS 137B (Green). Abaxial (lower) surface: RHS 138B (Green).
*Mature leaf texture.*—Adaxial (upper) surface: Glabrous. Abaxial (lower) surface: Pubescent.
*Leaf attachment.*—Petiolate.
*Petiole.*—Shape: Moderately sulcate. Length: Average is 0.55 cm (range is 0.47 cm to 0.62 cm). Width: Average is 0.096 cm (range is 0.073 cm to 0.14 cm). Surface: Glabrous (not pubescent). Color: Mostly RHS 146C (Yellow-green), with occasional tints of RHS 173A (Greyed Orange) or RHS 178A (Greyed Red).

Inflorescence:
*Inflorescence type.*—Raceme with the occasional panicle.
*Inflorescence diameter.*—Average is 8.6 cm (range is 6.7 cm to 10.5 cm).
*Inflorescence length: Average is* 11.8 cm (range is 6.0 cm to 18.6 cm).
*Number of flowers per inflorescence.*—4 to 10.
*Flower diameter.*—5.7 cm (range is 5.0 to 6.4 cm).
*Flower depth.*—Average is 1.1 cm (range is 0.88 cm to 1.5 cm).
*Type.*—Perfect, simple.
*Flowering season.*—Early spring through late spring; mid-April in Mills River, N.C.
*Lastingness of flower on the plant.*—7 to 21 days.
*Fragrance.*—Absent.
*Length at anthesis.*—Average is 6.0 cm (range is 3.6 cm to 8.6 cm).
*Self cleaning or persistent.*—Self-cleaning.
*Buds.*—Shape: Circular when viewed from above; Ventrally compressed rhomboidal when viewed in cross section. Length at balloon stage: Average is 1.1 cm (range is 0.80 cm to 1.5 cm). Diameter at balloon stage: Average is 1.2 cm (range is 0.98 cm to 1.41 cm). Color: RHS 155C (White).
*Sepal.*—Number: 5. Shape at anthesis: Oval to orbicular, fused below middle to base. Length at anthesis: Average is 0.38 cm (range is 0.32 cm to 0.44 cm). Width at anthesis: Average is 0.62 cm (range is 0.41 cm to 0.84 cm). Apex: Rounded. Margin: minutely irregularly crenulate. Color at anthesis, adaxial (upper) surface: Closest to RHS N155D (white). Color at anthesis, abaxial (lower) surface: Closest to RHS N155D (white).
*Petal.*—Number of petals per flower: Average is 5 (range is 5 to 6). Color, adaxial (upper) surface at anthesis: RHS 155C (White). Color, abaxial (lower) surfaces at anthesis: RHS 155C (White). Surface texture and appearance: Glabrous (not pubescent), soft, thin and lustrous (slightly shiny). Shape: Obovate. Apex: Obtuse. Base: Attenuate. Margin: Irregularly crenulate. Length: Average is 2.36 cm (range is 2.13 cm to 2.67 cm). Width: Average is 1.29 cm (range is 0.93 cm to 1.44 cm). Petals, fused or unfused: Unfused.
*Pedicel.*—Shape: Cylindrical, laterally compressed. Length: Average is 0.37 cm (range is 0.15 cm to 0.81 cm). Width: Average is 0.086 cm (range is 0.06 cm to 0.11 cm). Color: RHS 143A (Green). Surface texture: Glabrous (not pubescent).
*Peduncle.*—Shape: Cylindrical, laterally compressed. Length: Average is 1.19 cm from last flower to first pedicel (range is 0.33 cm to 1.72 cm). Width: Average is 0.17 cm at base (range is 0.14 cm to 0.20 cm). Color: Closest to RHS 143A (Green). Surface texture: Glabrous (not pubescent).

Reproductive organs:
*Stamen.*—Quantity per flower: Average is 31 (range is 28 to 36). Shape: Filament. Color: Translucent RHS 155C (White). Attachment: Dorsifixed. Anther: Length: Average is 0.11 cm (range is 0.082 cm to 0.137 cm). Width: Average is 0.063 cm (range is 0.044 cm to 0.071 cm). Shape: Ovoid. Color: RHS 11B (Yellow). Pollen color: RHS 11B (Yellow). Pollen amount: Moderate to copious, similar to parental lines.
*Pistil.*—Generally abortive.
*Ovary.*—Generally abortive or lacking.

Fruit:
*General.*—Fruit are infrequent; when present, a coccetum with 5 fused carples.
*Shape.*—Flattened sphere.
*Color.*—Initially RHS 139D (Green) eventually turning 177D (Brown).
*Length.*—1.2 cm.
*Width.*—1.5 cm.

Seed: No viable seed have been observed.

Disease and insect resistance: No significant disease or insect pests have been observed.

Genome size: Flow cytometry was conducted to determine DNA content which is directly correlated with ploidy level among closely related taxa. Holoploid, 2C DNA content was determined on newly expanded leaf tissue. Nuclei were extracted, stained with 4', 6-Diamidino-2-phenylindole (DAPI), and analyzed (minimum of 5,000 nuclei per sample) using a flow cytometer (PA-I, Partec, Münster, Germany). *Pisum sativum* L. 'Ctirad', with a known genome size of 8.75 pg was used as an internal standard. Mean (n=2), 2C DNA content for 'Blizzard' was 2.2±0.003 (SEM) pg, approximately twice the DNA content of either parent, demonstrating that 'Blizzard' is a polyploidy cytotype (see Table 1).

COMPARISON WITH PARENTAL AND COMMERCIAL VARIETIES

'Blizzard' is distinguished from the unnamed female parent, *Exochorda serratifolia* NCSU 2000-088 (unpatented) in that 'Blizzard' has a compact habit, has a smaller mature plant height and width, has a larger flower diameter, and a larger 2C genome size than the unnamed female parent *Exochorda serratifolia* NCSU 2000-088.

'Blizzard' is distinguished from the male parent *Exochorda×macrantha* 'The Bride' (unpatented) in that 'Blizzard' has an upright to rounded habit, has a larger flower diameter, and larger 2C genome size than the male parent 'The Bride'.

Table 1 shows the specific differences between 'Blizzard' and the unnamed female parent *Exochorda serratifolia* NCSU 2000-088 (unpatented) and *Exochorda×macrantha* 'The Bride' (unpatented).

TABLE 1

Additional comparisons of 'Blizzard' with parental lines

| | Taxa | | |
|---|---|---|---|
| Trait | 'Blizzard' | *E. serratifolia* | *E. × macrantha* 'The Bride' |
| Flower diameter | 5.0 cm to 6.4 cm | 2.8 cm to 4.5 cm | 3.1 cm to 3.7 cm |
| Petal number per flower | 5 to 6 | 5 to 11 | 5 or 6 |
| Pistil | Abortive | Fasciated ovary | Fasciated ovary |
| Plant habit | Compact shrub | Large shrub/ small tree | Open shrub |
| Plant shape | Upright/rounded | Open/spreading | Arching |
| Plant height | 1.2 m - 1.5 m | 2.5 m - 3.7 m | 1.5 m - 2.5 m |
| Plant width | 1.2 m - 1.5 m | 2.4 m - 3.7 m | 1.2 m - 2.4 m |
| Relative Genome Size (2C DNA content ± SEM) | 2.2 ± 0.003 pg | 1.1 ± 0.009 pg | 1.2 ± 0.005 pg |

When 'Blizzard' is compared to the commercial variety *E. serratifolia* 'Northern Pearls', 'Blizzard' is more compact with an upright/rounded form reaching approximately 1.5 m high, while 'Northern Pearls' has an arching vase shape and reaches 2.4 m.

I claim:

1. A new and distinct variety of pearlbush plant as described and shown herein.

* * * * *